(12) United States Patent
Park et al.

(10) Patent No.: US 12,296,747 B2
(45) Date of Patent: May 13, 2025

(54) SYSTEM FOR CONTROLLING INTERIOR LIGHTING OF MOBILITY DEVICE

(71) Applicants: HYUNDAI MOTOR COMPANY, Seoul (KR); KIA CORPORATION, Seoul (KR)

(72) Inventors: Sung Ho Park, Seoul (KR); Wan Hee Hong, Gunpo-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 398 days.

(21) Appl. No.: 17/875,702

(22) Filed: Jul. 28, 2022

(65) Prior Publication Data

US 2023/0133903 A1 May 4, 2023

(30) Foreign Application Priority Data

Nov. 3, 2021 (KR) ........................ 10-2021-0149932

(51) Int. Cl.
*B60Q 3/60* (2017.01)
*B60Q 3/20* (2017.01)
*B60Q 3/80* (2017.01)
*H05B 47/115* (2020.01)
*H05B 47/16* (2020.01)

(52) U.S. Cl.
CPC .............. *B60Q 3/60* (2017.02); *B60Q 3/20* (2017.02); *B60Q 3/80* (2017.02); *H05B 47/115* (2020.01); *H05B 47/16* (2020.01); *B60Q 2500/00* (2013.01)

(58) Field of Classification Search
CPC ........ H05B 47/16; H05B 47/11; H05B 45/20; H05B 45/00; H05B 45/10; H05B 45/12; H05B 45/18; H05B 45/22; H05B 45/28; H05B 47/105; H05B 47/165; H05B 47/115–13; B60Q 3/60; B60Q 3/20; B60Q 3/80; B60Q 2500/00; B60Q 2300/20; B60Q 2300/31; B60W 40/08; B60W 50/082; B60W 50/14; B60W 2040/0827; B60W 2040/0881; B60W 2050/143; B60Y 2400/90

See application file for complete search history.

(56) References Cited

U.S. PATENT DOCUMENTS 11,377,022 B2 * 7/2022 Pomish .................... B60Q 9/00
2022/0346207 A1 * 10/2022 Diamond .............. G01J 1/4204

FOREIGN PATENT DOCUMENTS

| JP | 2014-094708 A | | 5/2014 |
| JP | 2015221655 A | * | 12/2015 |
| JP | 6260453 B2 | | 1/2018 |
| JP | 6848687 B2 | | 3/2021 |
| KR | 10-2202016 B1 | | 1/2021 |

OTHER PUBLICATIONS

Translation of JP 2015221655 A (Year: 2015).*

* cited by examiner

*Primary Examiner* — Renan Luque
(74) *Attorney, Agent, or Firm* — MCDONNELL BOEHNEN HULBERT & BERGHOFF LLP

(57) ABSTRACT

A system for controlling interior lighting of a mobility device may change a lighting environment inside a mobility device based on outside environmental factors and the state of an occupant, thereby improving an interior aesthetic property, ensuring the occupant's convenience, and enabling safe traveling.

18 Claims, 5 Drawing Sheets

SYSTEM FOR CONTROLLING INTERIOR LIGHTING OF MOBILITY DEVICE

CROSS REFERENCE TO RELATED APPLICATIONS

This application is based on and claims priority under 35 U.S.C. 119 to Korean Patent Application No. 10-2021-0149932, filed on Nov. 3, 2021, in the Korean Intellectual Property Office, the disclosure of which is herein incorporated by reference in its entirety.

BACKGROUND

1. Field

The present disclosure relates to a system for controlling interior lighting of a mobility device, where the system changes a lighting environment inside a mobility device based on outside environmental factors and the state of an occupant, thereby improving an interior aesthetic property and ensuring the occupant's convenience.

2. Description of the Prior Art

Typically, a mobility device is required to have various types of convenience means, which can provided a stable and comfortable riding state to a user, in addition to functioning as a moving means.

An interior light for a mobility device, which is one of the convenience means, is advancing from merely illuminating the inside of a vehicle to providing a comfortable and cozy atmosphere to a driver and an occupant.

However, the interior light is configured to emit light while the brightness is fixed to an initial designed brightness. That is, use of the interior of a mobility device is increased, but light emitted by the interior light has fixed color temperature and brightness. Therefore, the usability of the interior light may be decreased.

In this way, the interior light is configured to be merely turned on or off so as to emit light or not to emit light, and thus it is difficult to use the interior light in accordance with the state and condition of the occupant. Therefore, the activity of a user in the mobility device may be restricted.

The above descriptions regarding background technologies have been made only to help understanding of the background of the present disclosure, and are not to be deemed by those skilled in the art to correspond to already-known prior arts.

SUMMARY

The present disclosure has been made in order to solve the above-mentioned problems in the prior art, and it is an aspect of the present disclosure to provide a system for controlling interior lighting of a mobility device, where the system changes a lighting environment inside a mobility device based on outside environmental factors and the state of an occupant, thereby improving an interior aesthetic property and ensuring the occupant's convenience.

In accordance with an aspect of the present disclosure, a system for controlling interior lighting of a mobility device may include a lighting module disposed in the mobility device and configured to emit light, the color temperature and illuminance of the light being adjustable, an environment information collector configured to collect information about environmental factors outside the mobility device, an occupant information collector configured to collect information about an occupant riding in the mobility device, and a controller configured to control the lighting module to operate at a color temperature and illuminance, pre-stored based on the outside environment information and the occupant information.

The environment information collector may collect outside-temperature information, and the controller may store color temperatures based on multiple preconfigured outside temperature ranges, and may determine the color temperature of the lighting module, based on an outside temperature that is input through the environment information collector.

The controller may classify the temperature ranges into a low-temperature range, a middle-temperature range, and a high-temperature range, and may determine the color temperature to be warm white in the low-temperature range, natural white in the middle-temperature range, and cool white in the high-temperature range.

The occupant information collector may identify the occupant riding in the mobility device, and the controller may control the lighting module to emit light having the determined color temperature and illuminance when the occupant is riding in the mobility device.

The occupant information collector may collect information about a position in which the occupant is sitting in the mobility device, and the controller may control the lighting module to emit light to only a region in which the occupant is positioned.

The controller may control the lighting module to be turned off when the mobility device switches to a traveling state.

The occupant information collector may determine an action mode required by the occupant, and the controller may pre-store color temperatures based on action modes, and, when an action mode is determined through the occupant information collector, may determine a color temperature based on the action mode.

The controller may classify the action mode into a rest mode, an entertainment viewing mode, a reading mode, and a business mode, and may determine the color temperature to be warm white in the rest mode, natural white in the entertainment viewing mode, and cool white in the reading mode and the business mode.

The controller may store color temperatures for sunrise and sunset according to time zones, and may determine a color temperature based on sunrise and sunset time zones for each position.

The environment information collector may collect illuminance information outside the mobility device, and the controller may store the illuminance of light emitted from the lighting module according to multiple preconfigured outside illuminance ranges, and may determine, based on a current outside illuminance, the illuminance of the lighting module.

The controller may control the illuminance of the lighting module to be increased as outside illuminance becomes higher, and may control the illuminance of the lighting module to be reduced as the outside illuminance becomes lower.

The occupant information collector may collect information about the state of the occupant, and the controller may pre-store color temperatures and illuminance based on the state of the occupant, and may control, when the occupant is in a sleepy state, the lighting module to have a predetermined color temperature and brightness according to the sleepy state.

The controller may control the color temperature and the brightness to be lowered when the mobility device autonomously travels.

The controller may control the lighting module to have a lowered color temperature and brightness or to be turned off during control based on the sleepy state.

The controller may control the lighting module to have a color temperature and brightness preconfigured for sleepiness prevention when the mobility device is manually traveled and when a rider is a driver.

The controller may increase the color temperature and the brightness when the driver is a sleepy state.

The controller may control the lighting module such that light having a color temperature and brightness preconfigured for sleepiness prevention is emitted to the entire interior of the mobility device when the state of the driver does not return from the sleepy state to a normal state for a predetermined time or longer.

The controller may transmit a warning sound to the interior of the mobility device when the state of the driver does not return from the sleepy state to the normal state for the predetermined time or longer.

The lighting module may be configured such that the emission direction of light is adjusted.

With the structure as described above, the system for controlling interior lighting of a mobility device may change a lighting environment inside a mobility device based on outside environmental factors and the state of an occupant, thereby improving an interior aesthetic property, ensuring the occupant's convenience, and enabling safe traveling.

BRIEF DESCRIPTION OF THE FIGURES

The above and other aspects, features, and advantages of the present disclosure will be more apparent from the following detailed description taken in conjunction with the accompanying drawings, in which.

DETAILED DESCRIPTION

Hereinafter, a system for controlling interior lighting of a mobility device according to an exemplary embodiment of the present disclosure will be described with reference to the accompanying drawings.

Figure 1:
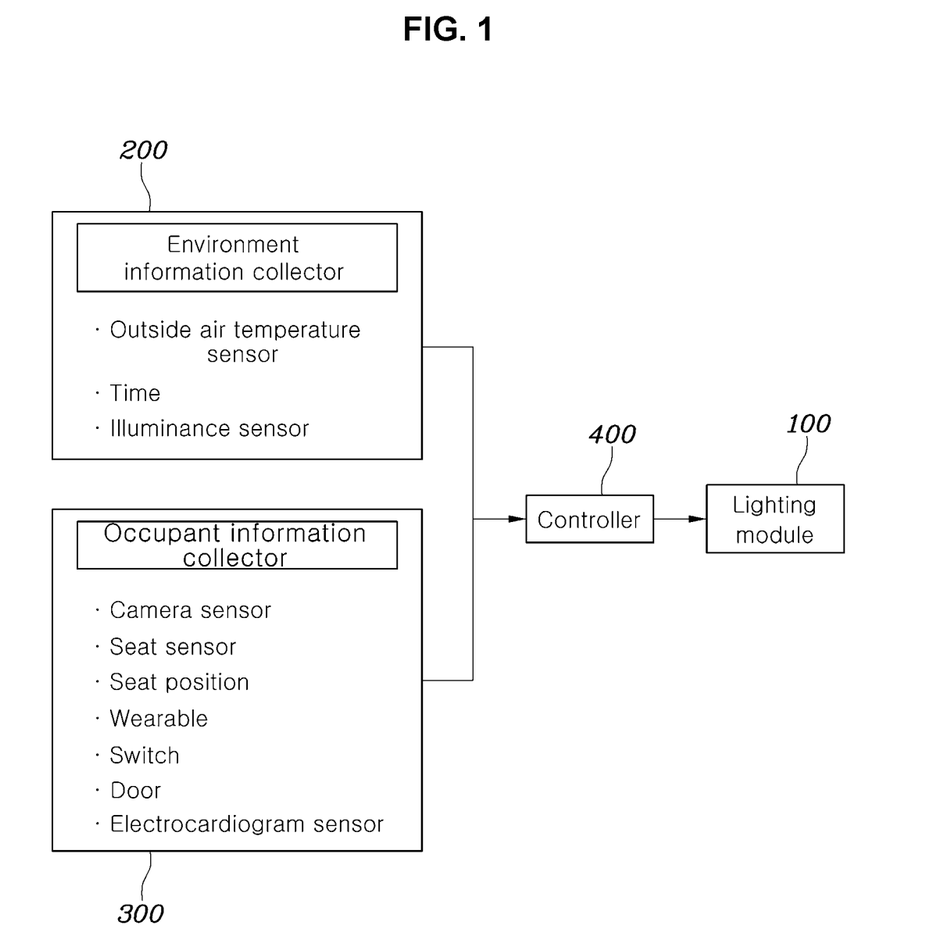
FIG. 1 illustrates elements of a system for controlling interior lighting of a mobility device according to the present disclosure.
Figure 2:
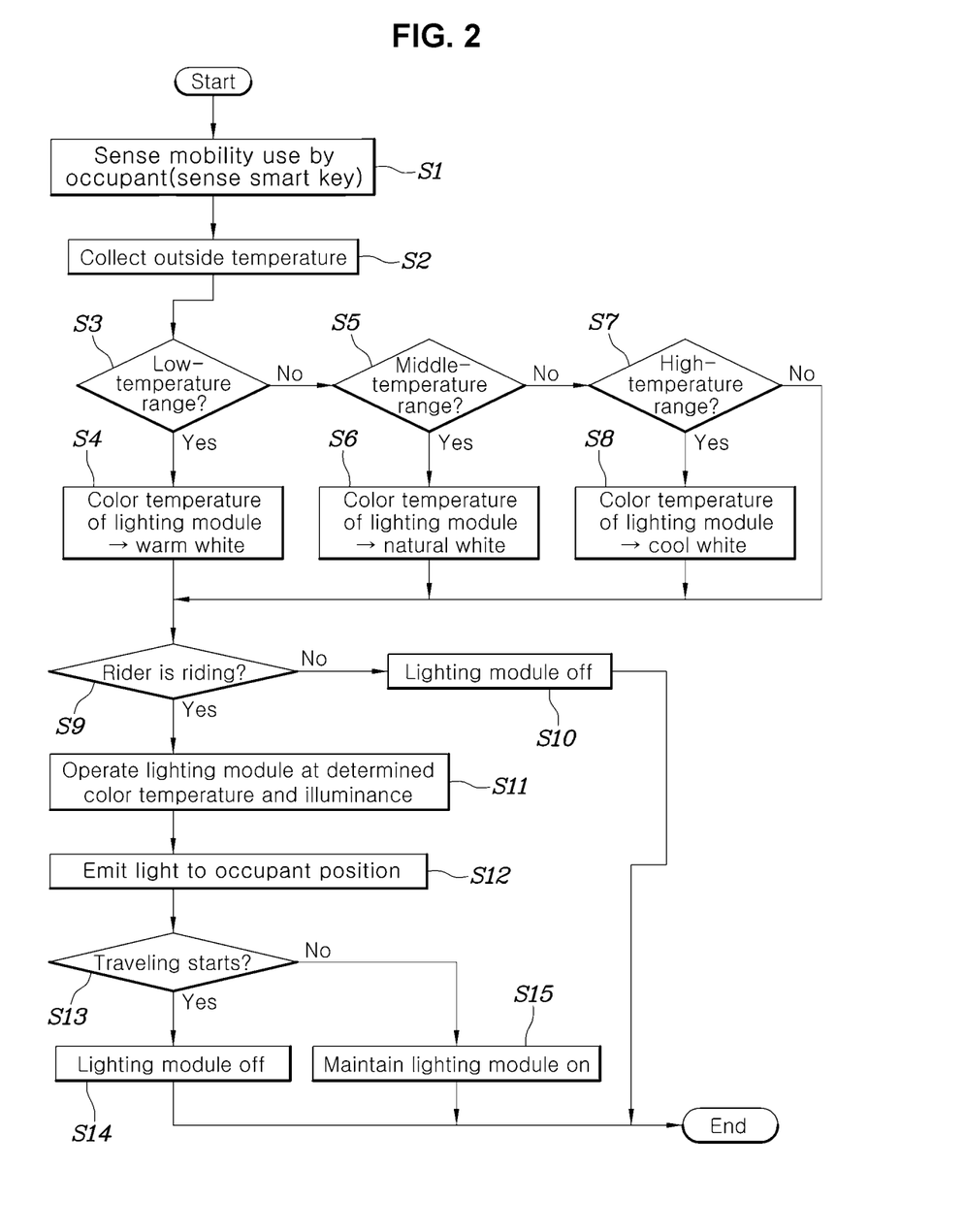
FIG. 2 is a flowchart regarding controlling interior lighting of a mobility device, based on an outside temperature.
Figure 3:
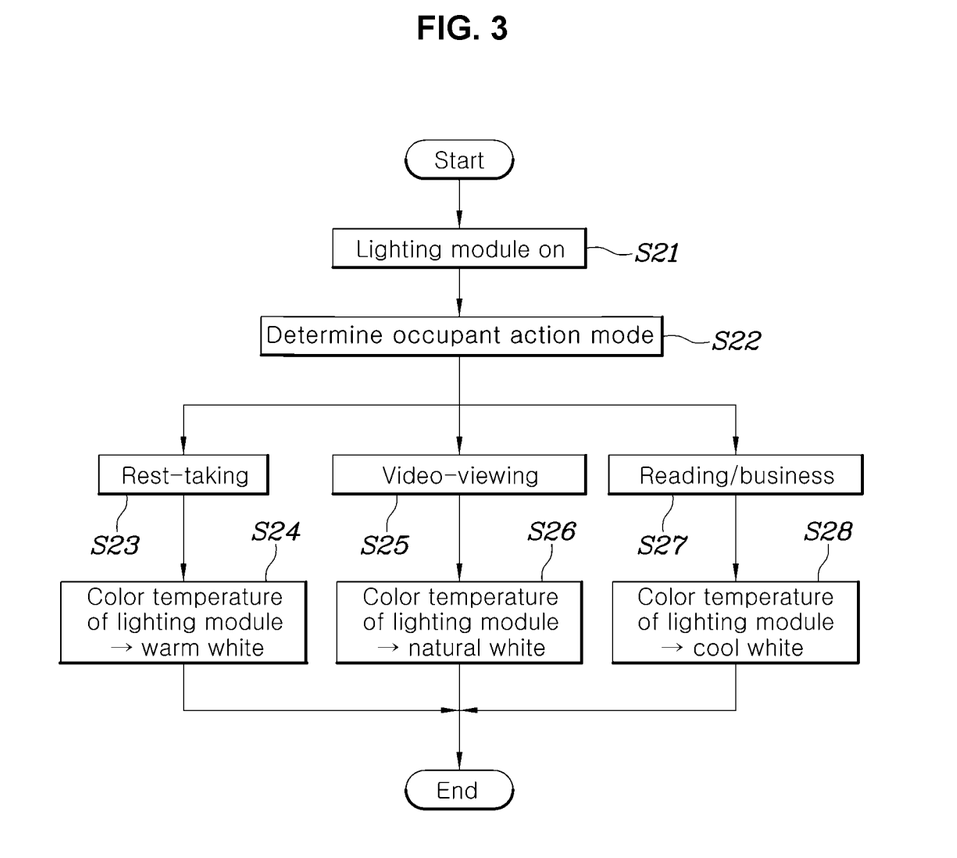
FIG. 3 is a flowchart regarding controlling interior lighting of a mobility device, based on an action mode of an occupant.
Figure 4:
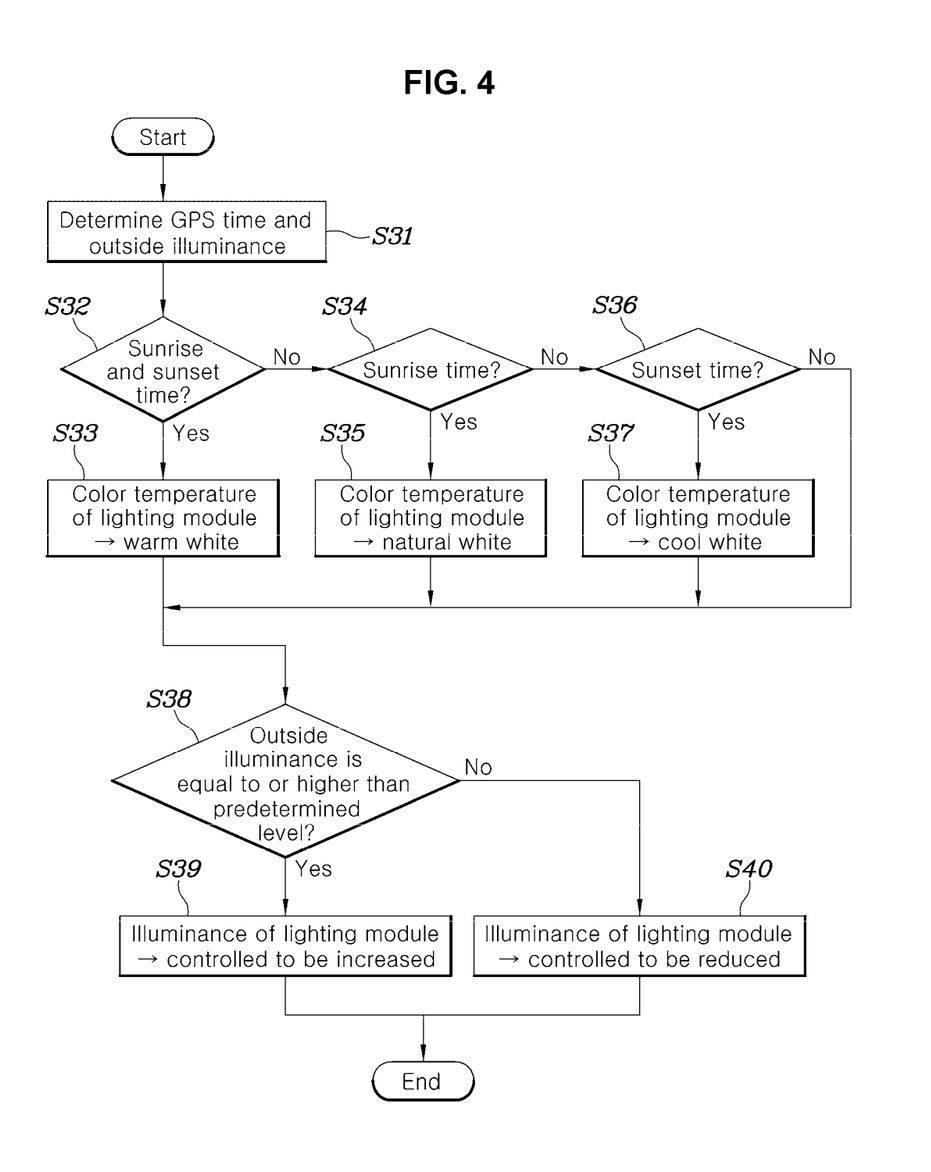
FIG. 4 is a flowchart regarding controlling interior lighting of a mobility device, based on time and illuminance.
Figure 5:
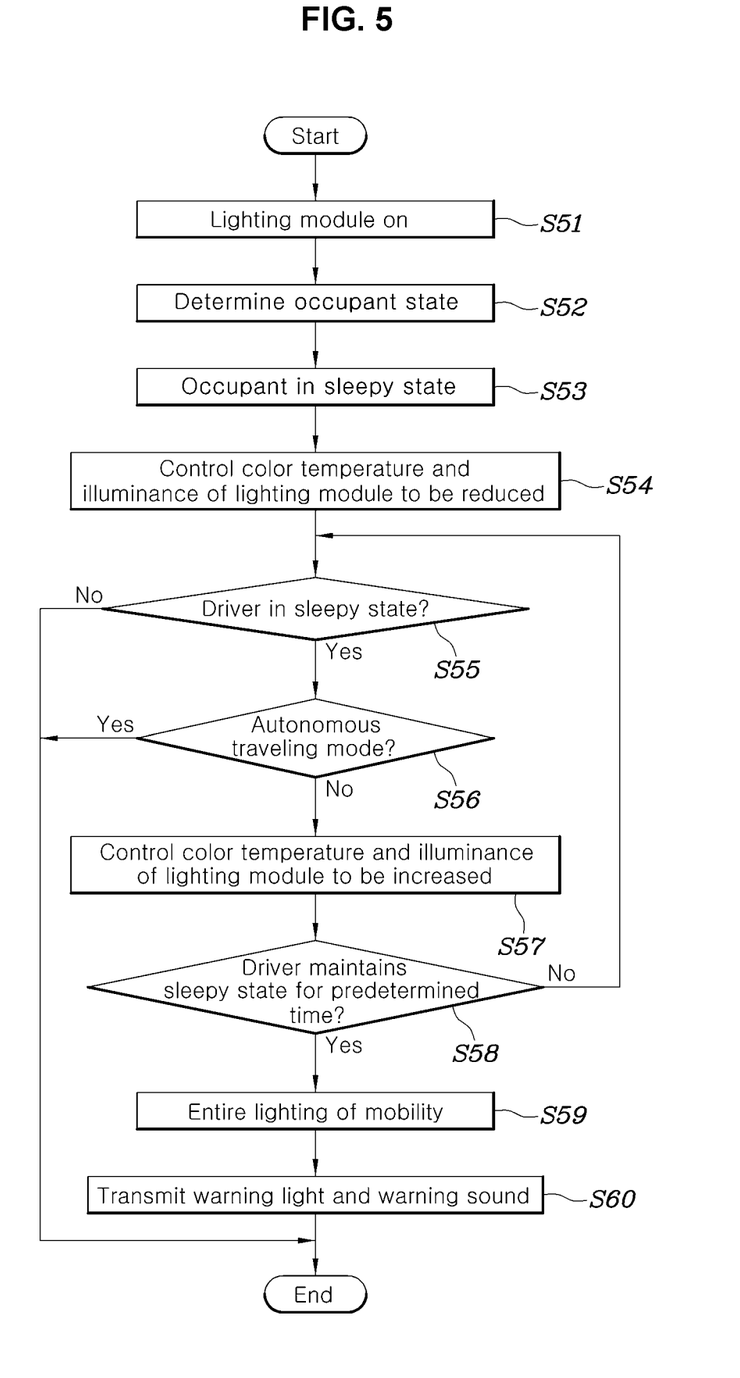
FIG. 5 is a flowchart regarding controlling interior lighting of a mobility device, based on the state of an occupant.

FIG. 1 illustrates elements of a system for controlling interior lighting of a mobility device according to the present disclosure. FIG. 2 is a flowchart regarding controlling interior lighting of a mobility device, based on an outside temperature. FIG. 3 is a flowchart regarding controlling interior lighting of a mobility device, based on an action mode of an occupant. FIG. 4 is a flowchart regarding controlling interior lighting of a mobility device, based on time and illuminance. FIG. 5 is a flowchart regarding controlling interior lighting of a mobility device, based on the state of an occupant.

As illustrated in FIG. 1, a system for controlling interior lighting of a mobility device, according to the present disclosure, may include a lighting module 100 disposed in the mobility device and configured to emit light such that the color temperature and illuminance of the light is adjusted, an environment information collector 200 configured to collect information about environmental factors outside the mobility device, an occupant information collector 300 configured to collect information about an occupant riding in the mobility device, and a controller 400 configured to control the lighting module to operate at a color temperature and illuminance, pre-stored based on the outside environment information and the occupant information.

The mobility device may have a space in which an occupant or baggage is picked up, and may be applied as a vehicle, an air mobility device, or the like.

The lighting module 100 may be installed in the mobility device so as to emit light in the inner space. Particularly, the lighting module 100 may be configured such that color temperature and illuminance are adjusted. Further, the lighting module 100 may be configured such that the emission direction of light is adjusted.

That is, the lighting module 100 may include multiple LEDs, and the color temperature and illuminance each LED may be adjusted by controlling the amount of current applied to the each LED.

Further, the lighting module 100 may include multiple LEDs and a lens on which light of the LEDs is incident and which is made of a silicone material so as to be flexibly deformed, whereby light of the LEDs may be refracted according to the deformation of the lens, and thus the emission position and the emission form of light may be changed. That is, the lens may be deformed to be unfolded or folded or may be deformed to tilt, and thus the emission position and the emission form of light may be changed. The lighting module 100 based on the adjustment of color temperature and illuminance and the adjustment of emission position is one embodiment, and may be applied in various implementation forms.

The environment information collector 200 may collect information about an environmental factor outside the mobility device. The environmental factor may include time, weather, outside temperature, outside illuminance, or the like.

The occupant information collector 300 may collect information about an occupant riding in the mobility device. The occupant information may include information about whether the occupant in the mobility device, the action of the occupant, the heart rate of the occupant, the eye-blink of the occupant, or the like.

Thus, the controller 400 may receive information from each of the environment information collector 200 and the occupant information collector 300, and may control an operation of the lighting module 100, based on the environment information and the occupant information. That is, the controller 400 may collate the environment information and the occupant information to determine color temperature and illuminance optimized for the interior of the mobility device, and may control the lighting module 100 to emit light at the determined color temperature and illuminance. Therefore, the interior aesthetic property may be improved by light emitted to the interior of the mobility device, and thus an occupant may feel comfortable through a lighting effect.

In this way, the present disclosure may change a lighting environment in a mobility device depending on outside lighting factors and the state of an occupant, thereby improving an interior aesthetic property, ensuring the occupant's convenience, and enabling safe traveling.

The present disclosure described above may be applied in various implementation forms.

The mobility device may communicate with a smart key of an occupant to recognize that the occupant will ride in the mobility device, and then may perform the following control.

The environment information collector 200 may collect outside-temperature information.

The controller 400 may store color temperatures based on multiple preconfigured outside temperature ranges, and may determine the color temperature of the lighting module 100, based on an outside temperature that is input through the environment information collector 200.

The environment information collector 200 may collect information about seasons and weather together with temperature through an outside air temperature sensor or GPS communication.

Like this, the present disclosure may adjust an interior color temperature of the mobility device, based on outside temperatures, seasons, and a weather, so that a lighting environment, which is not different from the outside environment, is made in the mobility device, and thus the occupant can feel psychologically comfortable when the occupant is riding in the mobility device.

Thus, color temperature according to an outside temperature range, seasons, and weather may be pre-stored in the controller 400, and when the corresponding condition is satisfied, the lighting module 100 may be controlled to operate at the predetermined color temperature, thereby minimizing a feeling of heterogeneity due to the difference between the interior and exterior of the mobility device.

That is, the controller 400 may classify the temperature ranges into a low-temperature range, a middle-temperature range, and a high-temperature range, and may determine the color temperature to be warm white in the low-temperature range, natural white in the middle-temperature range, and cool white in the high-temperature range.

In an example, the low-temperature range may be 15° C. or lower, the middle-temperature range may be 16° C. to 25° C., and the high-temperature range may be 26° C. or higher.

Thus, in relation to color temperatures preconfigured in the controller 400, a color temperature may be configured to be 2800K to 3500K in the low-temperature range so that warm white is implemented, a color temperature may be configured to be 4500K to 5000K in the middle-temperature range so that natural white is implemented, and a color temperature may be configured to be 5500K to 6500K in the high-temperature range so that cool white is implemented.

That is, in a situation such as winter including the low-temperature range, light emitted from the lighting module 100 may implement warm white, thereby making an occupant psychologically feel warm. In a situation such as summer including the high-temperature range, light emitted from the lighting module 100 may implement cool white, thereby making an occupant feel cool.

In this way, the present disclosure may vary the color temperature depending on an outside temperature range, thereby making an occupant feel comfortable when the occupant rides in the mobility device.

The occupant information collector 300 may identify the occupant riding in the mobility device, and the controller 400 may control the lighting module 100 to emit light having the determined color temperature and illuminance when the occupant is riding in the mobility device.

The occupant information collector 300 may determine whether a door is opened, or may determine whether an occupant is riding in the mobility device through a camera sensor or a seat sensor.

Like this, when an occupant is riding in the mobility device, the lighting module 100 may emit light at a color temperature and illuminance determined through the controller 400. Therefore, the present disclosure may provide a lighting effect when the occupant is riding in the mobility device, and may prevent power loss from being caused by emitting light when the occupant is not riding in the mobility device.

Particularly, the controller 400 may determine a color temperature and illuminance, based on the information collected by the environment information collector 200, before the occupant gets into the mobility device, such that light is emitted at a color temperature and illuminance according to an outside environment in the mobility device when the occupant gets into the mobility device.

The occupant information collector 300 may collect the position of the occupant in the mobility device, and the controller 400 may control the lighting module 100 to emit light to only a region in which the occupant is positioned.

That is, while the occupant is riding in the mobility device, light may be controlled to be emitted to only a region in which the occupant is positioned and to be not emitted to the remaining region in which the occupant is not positioned. Thus, the occupant's vision may be ensured in the mobility device, and power may be prevented to be unnecessarily consumed due to the region in which the occupant is not positioned.

The controller 400 may control the lighting module 100 to be turned off when the mobility device switches to a traveling state. That is, when light is continuously emitted from the lighting module 100 while traveling of the mobility device, a driver's vision may be obstructed, and thus the lighting module 100 may be controlled to be turned off. Alternatively, while traveling of the mobility device, an occupant's vision may be ensured by dimming the lighting module 100.

The above-described control of the controller 400 may be performed by steps S1 to S15 illustrated in FIG. 2. The present disclosure is not limited to the corresponding control, and various types of control may be applied based on an environmental factor and an occupant.

The occupant information collector 300 may determine an action mode required by the occupant.

The controller 400 may pre-store color temperatures based on action modes, and, when an action mode is determined through the occupant information collector 300, may determine a color temperature based on the action mode.

The occupant information collector 300 may determine the action mode required by the occupant through a position of a seat on which the occupant is sitting or through a command directly input by the occupant.

That is, the controller 400 may classify the action mode into a rest mode, an entertainment viewing mode, a reading mode, and a business mode, and may determine the color temperature to be warm white in the rest mode, natural white in the entertainment viewing mode, and cool white in the reading mode and the business mode.

Thus, when an action mode required by an occupant is determined, the controller 400 may determine a color temperature suitable for the action of the occupant, and may control the lighting module 100 to emit light at the determined color temperature.

When the occupant's action mode is the rest mode, the controller 400 may control light of the lighting module 100 to be implemented as warm white. When the occupant's action mode is the entertainment viewing mode such as video viewing, the controller 400 may control light of the lighting module 100 to be implemented as natural white. When the occupant's action mode is the reading mode or the business mode, the controller 400 may control light of the lighting module 100 to be implemented as cool white.

Thus, the present disclosure may control light suitable for an occupant's action to be emitted based on the occupant's action, thereby improving the occupant's convenience in the mobility device.

The above-described control of the controller 400 may be performed by steps S21 to S28 illustrated in FIG. 3. The present disclosure is not limited to the corresponding control, and various types of control may be applied based on an environmental factor and an occupant.

The controller 400 may store color temperatures for sunrise and sunset according to time zones, and may determine a color temperature based on sunrise and sunset time zones for each position.

The controller 400 may pre-store color temperature according time zones, and thus an occupant in the mobility device may recognize the passage of time. Particularly, the controller 400 may change the color temperature depending on sunrise and sunset according to time zones so that a lighting effect in the mobility device is also changed depending on the color temperature of the outside that is changed depending on the position of the sun. Further, a difference in the influence of sunrise and sunset may also be caused by the position of the mobility device. The controller 400 may receive GPS information to collect information about the position of the mobility device, sunrise, and sunset and determine a color temperature, thereby improving a lighting effect.

Further, the environment information collector 200 may collect illuminance information outside the mobility device.

The controller 400 may store the illuminance of light emitted from the lighting module 100 according to multiple preconfigured outside illuminance ranges, and may determine, based on a current outside illuminance, the illuminance of the lighting module 100.

The environment information collector 200 may collect illuminance information of the outside through an illuminance sensor.

Thus, the present disclosure may adjust the interior illuminance of the mobility device, based on the outside illuminance, to make, in the mobility device, a lighting environment which is not different from the outside environment, thereby making an occupant feel comfortable.

Thus, multiple outside illuminance ranges may be pre-stored in the controller 400, and when each illuminance is reached, the controller 400 may operate the lighting module 100 at an illuminance determined based on the corresponding illuminance range, thereby minimizing a feeling of heterogeneity due to the difference between the interior and exterior of the mobility device.

Accordingly, the controller 400 may control the illuminance of the lighting module 100 to be increased as the outside illuminance becomes higher, and may control the illuminance of the lighting module 100 to be reduced as the outside illuminance becomes lower.

When the outside illuminance is high, the controller 400 may control the illuminance of the lighting module 100 to be increased, thereby maintaining a lighting effect according to the determined color temperature. Further, when the outside illuminance is low, the controller 400 may control illuminance of the lighting module 100 to be reduced, thereby reducing a feeling of heterogeneity due to the difference between illuminance inside mobility device and illuminance outside the mobility device.

The above-described control of the controller 400 may be performed by steps S31 to S40 illustrated in FIG. 4. The present disclosure is not limited to the corresponding control, and various types of control may be applied based on an environmental factor and an occupant.

The occupant information collector 300 may collect information about the state of an occupant, and the controller 400 may pre-store color temperatures and illuminance based on the state of the occupant, and may control, when the occupant is in a sleepy state, the lighting module 100 to have a predetermined color temperature and brightness according to the sleepy state.

The occupant information collector 300 may collect information about changes in the occupant's body, including the health state of the occupant, through a wearable worn by the occupant, a camera sensor, an electrocardiogram sensor disposed in a seat, etc.

The controller 400 may pre-store color temperatures and illuminance, based on the state of the occupant. When the occupant information collector 300 collates the eye blinking, the heart rate, etc. of the occupant and determines that the occupant is in a sleepy state, the controller 400 may operate the lighting module 100 at a color temperature and brightness according to the sleepy state.

The controller 400 may differently perform control based on the sleepy state depending on whether the occupant is a driver or a passenger sitting on another seat or the traveling mode of the mobility device.

Specifically, when the mobility device autonomously travels, the controller 400 may control the color temperature and the brightness to be lowered.

When the mobility device autonomously travels, a driver or a passenger is not directly involved in the traveling, and thus the controller 400 may control the mobility device to stably travel.

Therefore, the controller 400 may control the lighting module 100 to have a lowered color temperature and brightness or to be turned off during control based on the sleepy state. That is, when the occupant is in the sleepy state while the mobility device autonomously travels, the controller 400 may control the lighting module 100 to have a lowered color temperature and brightness or to be turned off, thereby enabling the occupant to sleep soundly and thus improving satisfaction obtained by taking a rest.

When the mobility device is manually traveled and when the occupant is a driver, the controller 400 may control the lighting module 100 to have a color temperature and brightness preconfigured for sleepiness prevention. That is, when it is determined that the driver is in a sleepy state in a manual traveling state in which the driver directly controls the mobility device, the controller 400 may control the lighting module 100 to operate at a color temperature and brightness configured for sleepiness prevention.

When the driver is a sleepy state, the controller 400 may increase the color temperature and the brightness. That is, the color temperature and the illuminance for sleepiness prevention may be controlled such that the color temperature is implemented as cool white and the illuminance is increased. Further, the controller 400 may control light of the lighting module 100 to be focused on the driver's position. Therefore, the driver may recognize sleepiness through light emission, and thus a traveling accident may be prevented.

When the state of the driver does not return from the sleepy state to a normal state for a predetermined time or longer, the controller 400 may control the lighting module such that light having a color temperature and brightness preconfigured for sleepiness prevention is emitted to the entire interior of the mobility device.

That is, when the driver continuously remains in the sleepy state although the color temperature and brightness has been controlled based on the sleepy state of the driver, the controller 400 may control light of the lighting module 100 to be emitted to the entire interior of the mobility device.

The predetermined time configured in the controller 400 may be configured to be 1 to 3 seconds. When a predetermined time elapses since light of the lighting module 100 has been emitted to the driver at a color temperature and illuminance according to the sleepy state, light of the lighting module 100 may be emitted to the entire interior of the mobility device at an increased color temperature and illuminance so that other occupants in addition to the driver can recognize and cope with the sleepy state.

Further, when the state of the driver does not return from the sleepy state to the normal state for the predetermined time or longer, the controller 400 may transmit a warning sound to the interior of the mobility device. In addition, the controller 400 may flash an emergency light of the mobility device, thereby enabling a surrounding mobility device to avoid an accident caused by the driver's sleepiness.

In this way, the controller 400 may transmit a warning sound or warning light such that the driver returns from the sleepy state to the normal state, thereby maintaining safe traveling. Subsequently, when the heart rate, eye blinking, or the like of the drive returns to the normal state through the occupant information collector 300, the controller 400 may control the operation of the lighting module 100 to be normalized.

The above-described control of the controller 400 may be performed by steps S51 to S60 illustrated in FIG. 5. The present disclosure is not limited to the corresponding control, and various types of control may be applied based on an environmental factor and an occupant.

With the structure as described above, the system for controlling interior lighting of a mobility device may change the lighting environment in the mobility device depending outside environmental factors and the state of an occupant, thereby improving an interior aesthetic property, ensuring the occupant's convenience, and enabling safe traveling.

The present disclosure has been illustrated and described in relation to specific embodiments. However, it will be obvious to those skilled in the art that the present disclosure can be variously modified and changed without departing from the technical sprit of the present disclosure provided in the following claims.

The invention claimed is:

1. A system for controlling interior lighting of a mobility device, the system comprising:
a lighting module positioned in the mobility device and configured to emit light, a color temperature, and illuminance of the light, wherein the color temperature and illuminance of the light are adjustable;
an environment information collector configured to collect information about environmental factors outside the mobility device;
an occupant information collector configured to collect information about an occupant riding in the mobility device; and
a controller configured to control the color temperature and illuminance of the lighting module according to pre-stored color temperatures and illuminances based on the outside environment information and the occupant information;
wherein the environment information collector is configured to collect outside-temperature information; and
wherein the controller is configured to store color temperatures based on multiple preconfigured outside temperature ranges, and determine a color temperature of the lighting module based on an outside temperature that is input through the environment information collector.

2. The system of claim 1, the controller is configured to classify the temperature ranges into a low-temperature range, a middle-temperature range, and a high-temperature range, and wherein the color temperature is warm white in the low-temperature range, natural white in the middle-temperature range, and cool white in the high-temperature range.

3. The system of claim 1, wherein the occupant information collector is configured to identify the occupant riding in the mobility device, and
the controller is configured to control the lighting module to emit light having the determined color temperature and illuminance when the occupant is riding in the mobility device.

4. The system of claim 1, wherein the occupant information collector is configured to collect information about a position in which the occupant is sitting in the mobility device, and
the controller is configured to control the lighting module to emit light to only a region in which the occupant is positioned.

5. The system of claim 1, wherein the controller is configured to turn off the lighting module when the mobility device switches to a traveling state.

6. The system of claim 1, wherein the occupant information collector is configured to determine an action mode required by the occupant, and
the controller is configured to pre-store color temperatures based on action modes, and, when an action mode is determined through the occupant information collector, determine a color temperature based on the action mode.

7. The system of claim 6, wherein the controller is configured to classify the action mode into a rest mode, an entertainment viewing mode, a reading mode, and a business mode, and wherein the color temperature is warm white in the rest mode, natural white in the entertainment viewing mode, and cool white in the reading mode and the business mode.

8. The system of claim 1, wherein the controller is configured to store color temperatures for sunrise and sunset according to time zones, and to determine a color temperature based on sunrise and sunset time zones for each position.

9. The system of claim 1, wherein the environment information collector is configured to collect illuminance information outside the mobility device, and
the controller is configured to store illuminance of light emitted from the lighting module according to multiple preconfigured outside illuminance ranges, and to determine, based on current outside illuminance, illuminance of the lighting module.

10. The system of claim 9, wherein the controller is configured to increase the illuminance of the lighting module as outside illuminance becomes higher, and to reduce the illuminance of the lighting module as the outside illuminance becomes lower.

11. The system of claim 1, wherein the occupant information collector is configured to collect information about a state of the occupant, and the controller is configured to pre-store color temperatures and illuminance based on the state of the occupant, and control, when the occupant is in a sleepy state, the lighting module to have a predetermined color temperature and brightness according to the sleepy state.

12. The system of claim 11, wherein the controller is configured to lower the color temperature and the brightness when the mobility device autonomously travels.

13. The system of claim 11, wherein the controller is configured to control the lighting module to have a lowered color temperature and brightness, or to be turned off based on the sleepy state.

14. The system of claim 11, wherein the controller is configured to control the lighting module to have a color temperature and brightness preconfigured for sleepiness prevention when the mobility device is manually traveled and when a rider is a driver.

15. The system of claim 14, wherein the controller is configured to increase the color temperature and the brightness when the driver is a sleepy state.

16. The system of claim 15, wherein the controller is configured to control the lighting module such that light having a color temperature and brightness preconfigured for sleepiness prevention is emitted to an entire interior of the mobility device when a state of the driver does not return from the sleepy state to a normal state for a predetermined time or longer.

17. The system of claim 15, wherein the controller is configured to transmit a warning sound to the interior of the mobility device when the state of the driver does not return from the sleepy state to the normal state for the predetermined time or longer.

18. The system of claim 1, wherein the lighting module is configured such that an emission direction of light is adjusted.

* * * * *